(12) United States Patent
Castro et al.

(10) Patent No.: US 11,077,150 B2
(45) Date of Patent: Aug. 3, 2021

(54) METHODS AND COMPOSITIONS FOR TREATMENT OF EYE CONDITIONS

(71) Applicants: Travis Castro, Costa Mesa, CA (US); Tricia Scribner, Costa Mesa, CA (US); Massoumeh Kharazmi, Lake Forest, CA (US)

(72) Inventors: Travis Castro, Costa Mesa, CA (US); Tricia Scribner, Costa Mesa, CA (US); Mohammad Ali Kharazmi, Corona Del Mar, CA (US)

( * ) Notice: Subject to any disclaimer, the term of this patent is extended or adjusted under 35 U.S.C. 154(b) by 17 days.

(21) Appl. No.: 16/595,374

(22) Filed: Oct. 7, 2019

(65) Prior Publication Data
US 2020/0108101 A1    Apr. 9, 2020

Related U.S. Application Data

(60) Provisional application No. 62/743,314, filed on Oct. 9, 2018.

(51) Int. Cl.
| | |
|---|---|
| *A61K 35/50* | (2015.01) |
| *A61K 31/05* | (2006.01) |
| *A61K 31/352* | (2006.01) |
| *A61K 45/06* | (2006.01) |
| *A61K 31/4164* | (2006.01) |
| *A61K 35/28* | (2015.01) |
| *A61K 9/51* | (2006.01) |
| *A61K 9/00* | (2006.01) |
| *A61P 27/02* | (2006.01) |
| *A61K 35/44* | (2015.01) |
| *A61K 35/12* | (2015.01) |

(52) U.S. Cl.
CPC ............ *A61K 35/50* (2013.01); *A61K 9/0048* (2013.01); *A61K 9/5123* (2013.01); *A61K 9/5153* (2013.01); *A61K 9/5161* (2013.01); *A61K 31/05* (2013.01); *A61K 31/352* (2013.01); *A61K 31/4164* (2013.01); *A61K 35/28* (2013.01); *A61K 35/44* (2013.01); *A61K 45/06* (2013.01); *A61P 27/02* (2018.01); *A61K 2035/124* (2013.01)

(58) Field of Classification Search
CPC .......................... A61K 9/0048; A61K 31/352
See application file for complete search history.

(56) References Cited

U.S. PATENT DOCUMENTS

| | | | | |
|---|---|---|---|---|
| 8,865,685 | B2 * | 10/2014 | Gallois-Bernos | A61K 31/232 514/120 |
| 2004/0192647 | A1 * | 9/2004 | Babizhayev | A61K 31/07 514/57 |
| 2007/0264318 | A1 * | 11/2007 | Chapin | A61K 31/137 424/448 |
| 2011/0311491 | A1 * | 12/2011 | Edinger | A61P 1/14 424/93.7 |
| 2013/0029970 | A1 * | 1/2013 | Sprott | A61P 25/30 514/211.15 |
| 2016/0184259 | A1 * | 6/2016 | Anastassov | A61K 31/352 514/454 |

\* cited by examiner

*Primary Examiner* — Michael B. Pallay

(57) ABSTRACT

The invention includes compositions and methods of administering the compositions to improve the condition of damaged eye tissues. The compositions include cannabinoids such as cannabidiol and one or more of human stem cell products, lutein, and N-acetyl carnosine. The compositions include components that are encapsulated and may include a mixture of separately encapsulated materials. The methods include administering the compositions as drops to an affected eye.

18 Claims, No Drawings

METHODS AND COMPOSITIONS FOR TREATMENT OF EYE CONDITIONS

RELATED PATENT APPLICATION

This application claims the benefit of U.S. provisional patent application No. 62/743,314, filed on Oct. 9, 2018. The entire content of the provisional patent application is incorporated herein for all purposes.

FIELD OF THE INVENTION

This invention is in the field of treatment of the eyes due to injury, aging, degeneration, or disease.

BACKGROUND

This invention includes compositions and methods of administering the compositions to improve the condition of damaged eye tissues. The compositions include cannabinoids such as cannabidiol and one or more of human stem cell products, lutein, and N-acetyl carnosine. The compositions include components that are encapsulated and may include a mixture of separately encapsulated materials. The methods include administering the compositions as drops to an affected eye.

Eyes may be damaged by trauma, wound, burn, surgery, disease, compromised circulation, infarct, degeneration, aging, and other events or conditions. Tissues may also suffer environmental or disease-induced damage such as conjunctival inflammation and retinal overgrowth. Damage may arise from age-related macular degeneration, cataract, diabetic retinopathy, glaucoma, corneal neuropathic pain, and other conditions. Damaged tissue may heal naturally, but this process may be slow, uncomfortable, or incomplete. In some cases, the natural healing process produces a functional deficit such as reduced visual field, impaired visual acuity, "floaters" in the visual field, or scarring. There is a need to prevent or reduce discomfort during treatment of such conditions.

Healing of damaged or dysfunctional eye tissue may be impaired by a variety of insults including aging, injury, circulatory impairment, and nerve damage. As tissue ages, hormone levels change, and the structure of tissue often thins and weakens. Tissue fibroblasts may become less active and tissues becomes thinner and lose elasticity; as tissue thins, circulation can lessen, and innervation may become sparser or less responsive. Tissue can show a decrease in volume and elasticity. There is a need to prevent and reverse these conditions to maintain and recover healthy function.

The normal process of healing goes through a series of stages, such as that for wounded skin. In the wound healing process, injured tissue is repaired, specialized tissue is regenerated, and new tissue is reorganized. Three major phases are an inflammation stage of zero to three days, a proliferation stage of three to twelve days, and a remodeling phase of a few days to six months or more. In the inflammation phase, platelet aggregation and clotting form a matrix which traps plasma proteins and blood cells and induces the in-migration of various cells from surrounding tissues. In the cellular proliferation phase, new connective or granulation tissue and blood vessels form. In the remodeling phase, granulation tissue is replaced by a network of collagen and elastin fibers producing scar tissue. Each of these phases is at least partly dependent on signaling by growth factors produced by healing tissue and by adjacent tissue.

The remodeling phase may produce variable amounts of scar tissue or of repaired or regenerated tissue. This depends on the tissue location and on age: older mice repair injuries with less scarring at least partly due to suppression of stromal-derived factor 1 (SDF1) in the regenerating tissue (see Nishiguchi et al. Cell Reports 24, 3383-92 (2018)).

Eyes are sensitive to topically added materials, particularly oils or lipophilic compounds. Commercial eye drops include aqueous materials such as 0.4% polyethylene glycol 400 and 0.3% propylene glycol as lubricants for dry eyes with "inactive ingredients" of aminomethylpropanol, boric acid, hydroxypropyl guar, polyquaternium-1 0.001% preservative, potassium chloride, purified water, sodium chloride, and sorbitol. Jay et al. in Arch. Opthalmology 101:4, 591-3 (1983) reported topically applied $\Delta^9$-tetrahydrocannabinol (THC) in light mineral oil did not improve interocular pressure but did cause burning sensation, lid swelling, and withdrawal of volunteers from the trial. Eyes may thus be particularly sensitive to applied hydrophobic materials or oils.

Many materials may contribute to healing, regeneration, or protection of the eyes. These materials include cannabinoids, lipophilic vitamins or such as lutein, hydrophilic antioxidants such as N-acetyl carnosine, and cellular growth factors and cytokines.

Cannabinoids

Isolated compounds from the *cannabis* plant are called cannabinoids; there are at least one hundred distinct cannabinoids in the *cannabis* plant. Most cannabinoids are cyclic or poly cyclic and are hydrophobic. Cannabinoids include THC, cannabidiol (CBD), cannabichromene (CBC), cannabigerol (CBG), cannabidivarin (CBDV), among other compounds. THC has psychoactive effects; CBD, CBC, CBG, and CBDV have relatively little or no psychoactive effect. Many researchers have asserted medicinal values for cannabinoids, though these remain controlled substances under U.S. federal law. CBD is the highest concentration non-psychoactive cannabinoid, accounting for up to 40% of the plant's extract. The combination of CBD with other non-psychoactive cannabinoids isolated from plant extracts is sometimes known as "full spectrum CBD."

Some cannabinoids interact with the body through specific membrane-bound receptors. Cannabinoid receptor type 1 (CB1) receptors are found primarily in the brain, more specifically in the basal ganglia and in the limbic system, including the hippocampus and the striatum. CB1 receptors are also found in the cerebellum and in both male and female reproductive systems.

Both CB1 and cannabinoid receptor type 2 (CB2) receptors are found in the human eye. Straiker et al. in *Investigative Ophthalmology & Visual Science* 40, 2442-2448 (1999) reported CB1 receptors in the ciliary epithelium, the corneal epithelium, and endothelium of the anterior human eye. Strong-to-moderate levels of CB1 staining were found in the trabecular meshwork and Schlemm's canal. Moderate labeling was detected in the ciliary muscle and in the blood vessels of the ciliary body. Moderate-to-light labeling also was detected in the sphincter papillae of the anterior human eye. Staining for CB1 receptors also was detected in the retina: the two synaptic layers of the retina and the inner and outer plexiform layers were both moderately stained for CB1. In addition, moderate labeling was detected in the inner nuclear layer, and the ganglion cell layer. Strong labeling was detected in the outer segments of photoreceptors.

CB2 receptors are expressed in human retinal pigment epithelium cells human retinal pigment epithelial (RPE)

cells of the eye. Wei et al. in *Molecular Vision* 15, 1243-51 (2009) reported that both CB1 and CB2 receptors were upregulated in cultures of an RPE cell line when stressed with peroxides and that CB2 receptor agonists attenuate $H_2O_2$-induced cytotoxicity.

CB2 receptors are also found in the immune system, or in immune-derived cells with the greatest density in the spleen. CB2 receptors may be responsible for reported anti-inflammatory and possibly other therapeutic effects of *cannabis* seen in animal models.

Endogenous lipophilic ligands (endocannabinoids) including anandamide and 2-arachidonylglycerol also bind CB1 and CB2. Known endocannabinoids, unlike *cannabis*-sourced cannabinoids, are acyclic molecules. Anandamide binds to CB1 and, to a lesser extent, to CB2 receptors; 2-arachidonoylglycerol binds to both CB1 and CB2 receptors with similar affinity.

Schwitzer et al. reviewed the endocannabinoid system in the retina in Neural Plasticity Article ID 2916732 (2016). They reported that the retinal cannabinoid system might play a neuroprotective role in the retina. Oxidative stress is a key mechanism in the pathological process of age-related macular degeneration (AMD) and diabetic retinopathy (DR). In a cellular model of AMD, inhibition of CB1 receptors protected retinal pigment epithelium cells from oxidative damage. DR is characterized by an oxidative stress, a breakdown of the blood-retinal barrier, and a proinflammatory effect, which are associated with retinal neuronal death. In a rat model of DR, treatment with cannabidiol significantly reduced both oxidative stress and neurotoxicity and prevented retinal cell death. Consequently, exo-cannabinoids may be a relevant therapeutic strategy decreasing oxidative stress signaling and preventing neurodegeneration of retinal cells in AMD and DR. Schwitzer et al. concluded that the retinal protective role of exo-cannabinoids on both the structural and functional properties of retinal cells supports use of cannabinoids in retinal diseases as new therapeutic agents to prevent neurodegeneration and cell death.

CBD is the major nonpsychoactive ingredient in *cannabis*. It is reported to possess neuroprotective and anti-inflammatory effects. Various cannabinoids activate the endocannabinoid system, which consists of receptors, synthetic and degradative enzymes, and transporters.

Cannabidiol has low affinity for CB1 and CB2 receptors but appears to act as both an agonist and antagonist of CB2 receptors depending on concentration. This paradoxical action is likely due to indirect action on other receptors or enzymes that are functionally linked to the CB2 receptor. Cannabidiol interacts with many other, non-endocannabinoid signaling systems. At low micromolar to sub-micromolar concentrations, cannabidiol blocks equilibrative nucleoside transporter (ENT), the orphan G-protein-coupled receptor GPR55, and the transient receptor potential of melastatin type 8 (TRPM8) channel. Conversely, cannabidiol enhances the activity of the 5-$HT_{1a}$ receptor, the α3 and α1 glycine receptors, the transient receptor potential of ankyrin type 1 (TRPA1) channel and has a bidirectional effect on intracellular calcium. At higher micromolar concentrations, cannabidiol activates the nuclear peroxisome proliferator-activated receptor-γ and the transient receptor potential of vanilloid type 1 (TRPV1) and 2 (TRPV2) channels while also inhibiting cellular uptake and fatty acid amide hydrolase-catalyzed degradation of anandamide. Cannabidiol is also a potent antioxidant because of its multiple phenolic structures.

Ibrahim et al. in *PNAS* 102:8, 3093-8 reported that CB2 receptor activation inhibits acute, inflammatory, and neuropathic pain responses; CB2 receptor activation stimulates release from keratinocytes of β-endorphin, which acts at local neuronal μ-opioid receptors to inhibit nociception.

Cannabidiol has high lipophilicity ($K_{octanol-water}$~6-7) and consequently very low water solubility. This limits its availability in many formulations, particularly topical applications such as eyedrops. Cannabinoids, including THC, have been shown effective against eye conditions including glaucoma when injected into the eye, but the high lipophilicity of cannabinoids in general and CBD in particular makes less invasive topical application problematic. There is thus a need for a topical method of applying cannabinoids to treat eye conditions that is effective and without irritation.

Antioxidants

Cannabinoids have antioxidant activity in addition to receptor-based biological activity. Other materials, which may be either lipophilic or hydrophilic, may also advantageously provide antioxidant activity. Antioxidants generally act sacrificially: they are more readily oxidized than sensitive biological structures. Oxidizing agents, including peroxides, free radicals, and other reactive oxygen species, which might otherwise damage or destroy biological structures, instead may react with antioxidants so that both the oxidizing agents and the antioxidants are degraded. In some instances, antioxidants may help to restore an oxidizer-damaged biological structure by reducing the biological structure.

Lipophilic Antioxidants

CBD and other cannabinoids are strong antioxidants in lipophilic environments. The carotenoid vitamin lutein is also lipophilic and is found in the macula of the human retina. The polyene chain of lutein is susceptible to oxidative degradation by light or heat and normally reaches the macula through the systemic circulation. Dietary supplementation with lutein in patients with early AMD produced improvement in contrast sensitivity. Studies found a correlation between high diet content or high serum concentrations of lutein and zeaxanthin and a decrease in the risk of cataract. There may be a cataract prevention benefit for people with low dietary intake of lutein. Because lutein is very lipophilic, it is not applicable topically to the eyes in unaltered form.

Sabliov et al. US 2017/0216221 A1 disclosed application of lutein in eyedrops to treat or prevent cataracts. The lutein was packaged in an nanoparticle matrix of zein (the principal protein of corn) or a synthetic polymer such as poly(lactic-co-glycolic acid) (PLGA) together with a surfactant to produce particles in a size range of about 140 to 250 nm. Animal experiments successfully delivered the packaged lutein in a thermosensitive, bioadhesive gel to the eye in therapeutically effective amounts. The gel was formulated for prolonged retention following topical administration. While the packaged lutein had better stability than a lutein emulsion, more than 25% of the lutein had degraded after 30 days at room temperature. The stored particles more than doubled in size during this period. This rapid degradation limits the shelf life of any lutein eye drops. There is thus a need for a lutein topical eye formulation that has extended stability, particularly in combination with cannabinoid treatment.

U.S. Pat. No. 9,814,695 to Anastassov et al. discloses an ophthalmic solution comprising cannabinoids, specifically THC, CBD, and CBG in specific proportions in an aqueous solution for treatment of glaucoma. The ophthalmic solution comprised CBD and CBG dissolved in balanced saline solution for symptomatic relief of conjunctival inflammation. Anastassov et al. disclosed that, to facilitate dissolution of cannabinoids in the eye drop solution, cannabinoids may be encapsulated in liposomal capsules, may be freeze dried and dissolved in an alcohol solution to promote dissolution, or may also be complexed with β-cyclodextrin to increase dissolution rate in water-based solutions.

Anastassov et al. mentions alternate treatments including lutein but does not disclose or suggest combining lutein with CBD or co-encapsulating lutein with CBD. Nor does Anastassov et al. disclose or suggest combining CBD with any of aqueous antioxidants or cellular growth factors.

Hydrophilic Antioxidants

Hydrophilic antioxidants that may have value in topical eye treatment include at least lipoic acid, glutathione, and carnosines such as N-acetyl carnosine. Principle intracellular antioxidants of ascorbic acid and glutathione also protect tissue and may be incorporated in some embodiments.

U.S. Pat. No. 7,795,203 to Babizhayev discloses that N-acetyl carnosine converts into L-carnosine upon the topical ocular administration at a faster rate in the presence of a cellulose compound such as carboxymethylcellulose. Babizhayev et al. in *Clin Interv Aging* 4:31-50 (2009) reported on a nine-month trial of eye drops containing N-acetyl carnosine. The lead author's contact information is that of a manufacturer of such eye drops; he is a co-author for a large fraction of the papers with positive reports in this field. The report found that 75 symptomatic patients with age-related uncomplicated cataracts "generally showed an improvement in visual acuity . . . and a significant improvement in glare sensitivity". The same paper reported a "sharp increase in net earnings" and that an analysis of product sales to repeat purchasers suggested the eye drops were effective against a wide variety of eye conditions. Notwithstanding this report, Grover et al. in a literature examination review in *Mol Cell Biochem* 388:1-2, 173-83 (2014) reported that lubricant drops containing N-acetyl carnosine may be helpful in initial stages of cataracts. Neither Babizhayev nor Grover disclose or suggest a topical eye drop composition that combines N-acetyl carnosine with a cannabinoid with or without lutein or cellular growth factors.

Lipoic acid, also known as α-lipoic acid, is an organosulfur compound derived from octanoic acid. Lipoic acid contains two sulfur atoms connected by a disulfide bond and acts as a cofactor of the pyruvate dehydrogenase complex and in other enzymes. Lipoic acid has antioxidant and iron-chelating properties; when administered systemically, lipoic acid improved symptomatic diabetic polyneuropathy and may have potential benefits for geographic atrophy in dry age-related macular degeneration as well as other eye diseases. Sarezky et al. in *Clinical Opthamology* 10, 1899-1903 (2016) reported that, while higher doses were associated with some adverse effects, oral doses of up to 600 mg were well tolerated among elderly subjects.

U.S. Pat. No. 7,776,915 to Morariu discloses dermatological compositions and the topical application of such compositions for the prevention and/or treatment of damage to skin. The compositions contain a combination of a lipoic acid, a carnitine, and a carnosine. A two-plus page list of anti-inflammatory agents that may be useful in combination with the lipoic acid, carnitine, and carnosine formulation includes CBD. Morariu discloses inclusion of antioxidants including lutein but no disclosure is made of any composition that does not include a carnitine and a lipoic acid. Because oral administration of lipoic acid may have other systemic benefits (such as in treatment of symptomatic diabetic polyneuropathy), and reasonable doses are well tolerated, lipoic acid may be better administered systemically.

Further Morariu teaches the compositions are useful for treatment of the dermis but makes no mention of eyes other than for cosmetics such as eye shadow. There is thus a need for a carnosine topical eye formulation that does not include lipoic acid, particularly in combination with cannabinoid with or without lutein or cellular growth factors.

Cellular Growth Factors

One approach to improve tissue healing is to treat the damaged tissue with one or more cellular growth factors. Many tissues respond to mixtures of growth factors to encourage regeneration. In some cases, the growth factors may be produced by a cell culture as a conditioned medium. For example, US 2012/0065129 A1 to Park et al. asserts that a culture medium of adipose-derived stem cells and growth factors isolated from the culture medium can be advantageously applied for wound healing. The applied growth factors are intended to recruit and support replication-competent cells to repair the damage. Such cellular growth factors may also be beneficial for regeneration of eye tissue.

The mode of action of cellular growth factors, cannabinoids, and antioxidants are different. Combinations of these materials in a single composition may produce complementary beneficial effects not available if the materials were administered separately. For example, eyes are sensitive to pain; the cornea, in the front of the eye, has more pain receptors per square inch than anywhere else in the body. Injury to and healing of tissue damage may be painful, and the surrounding tissue may be damaged by the inflammation of treatment regime itself. As discussed above, CB2 receptor activation stimulates release from keratinocytes of β-endorphin, which acts at local neuronal μ-opioid receptors to inhibit nociception. There is thus a need for a treatment composition that relieves such pain during treatment.

SUMMARY

In embodiments, the invention includes eye treatment compositions and a method of treatment using the compositions.

In one embodiment, the treatment composition includes a first plurality of capsules suspended in an aqueous carrier. The first plurality of capsules includes a cannabinoid, which may include CBD, a mixture of non-psychoactive cannabinoids, or THC. The first plurality of capsules may also include a lipophilic antioxidant co-encapsulated with the cannabinoid.

The treatment composition may further comprise a second plurality of capsules suspended in the aqueous carrier. The second plurality of capsules may include one or more of an aqueous antioxidant or cellular growth factors.

The cellular growth factors may comprise a stem cell enriched culture medium. human hematopoietic stem cell, a human endothelium-derived stem cell, a human adipose-derived stem cell, a human tooth mesenchyme-derived stem cell, or a human placenta-derived stem cell.

The invention includes an eye treatment composition including a plurality of nanocapsules with a cannabinoid and a lutein co-dispersed in the plurality of nanocapsules. The nanocapsules may be suspended in an aqueous carrier. The cannabinoid may be cannabidiol.

The eye treatment composition may also include an aqueous antioxidant mixed with the aqueous carrier. The eye treatment composition may also include a stem cell conditioned medium mixed with the aqueous carrier.

The inventive compositions may include a plurality of microcapsules suspended in the aqueous carrier. The microcapsules have one or more of N-acetyl carnosine and a conditioned medium. The nanocapsules may have a median size in the range of 50 to 250 nm, and the microcapsules may have a median size in the range of 500 nm to 5 μm.

The encapsulated conditioned medium may be derived from a culture of one or more of a human hematopoietic stem cell, a human endothelium-derived stem cell, a human adipose-derived stem cell, a human tooth mesenchyme-derived stem cell, or a human placenta-derived stem cell.

In other embodiments, the invention includes an eye treatment composition having a first plurality of nanocapsules and a plurality of microcapsules. The nanocapsules and the microcapsules are suspended in an aqueous carrier. A cannabinoid, such as CBD or THC, is dispersed in the first plurality of nanocapsules and a stem cell conditioned medium is dispersed in the plurality of microcapsules. The nanocapsules may have a median size in the range of 50 to 250 nm, and the microcapsules may have a median size in the range of 500 nm to 5 μm.

In embodiments, lutein may be dispersed in a second plurality of nanocapsules or may be co-dispersed with the cannabinoid in the first plurality of nanocapsules.

In embodiments, the invention also includes an eye treatment composition having a plurality of nanocapsules and a plurality of microcapsules suspended in an aqueous carrier. A cannabinoid is dispersed in the nanocapsules, and N-acetyl carnosine is dispersed in the microcapsules. The nanocapsules may have a median size in the range of 50 to 250 nm, and the microcapsules may have a median size in the range of 500 nm to 5 μm.

In other embodiments, the eye treatment composition includes a plurality of nanocapsules with a cannabinoid, such as CBD or THC, dispersed within the nanocapsules. An aqueous carrier suspends the nanocapsules and includes a vasoconstrictor and a lubricant. The plurality of nanocapsules has a median size in the range of 50 to 250 nm. In some of these embodiments, the lubricant for dry eyes may be glycerol, polyethylene glycol 400, propylene glycol, or hydroxypropyl methylcellulose.

Embodiments may also include ingredients to reduce the visible appearance of redness in the conjunctiva such as a vasoconstrictor or decongestant to constrict blood vessels.

In other embodiments, the invention includes a method of treating an eye condition including applying an effective amount of any of the described compositions to an affected eye.

DETAILED DESCRIPTION

The invention includes methods of treating conditions, diseases, or dysfunction of the eye and compositions useful in such methods. In embodiments, the compositions include encapsulated cannabinoids such as CBD and one or more of lutein, n-acetyl carnosine, conditioned stem cell culture medium, vasoconstrictors, lubricants and support ingredients such as saline or boric acid. In other embodiments, the invention includes methods treating an affected area of a human with one or more of the compositions.

In some embodiments, the invention includes compositions comprising a cannabinoid, such as CBD, and lutein co-encapsulated in nanocapsules.

In some embodiments, the invention includes compositions comprising a cannabinoid, such as CBD or THC, encapsulated in nanocapsules and combined with one or more of N-acetyl carnosine or conditioned stem cell culture medium. The N-acetyl carnosine or the conditioned stem cell culture medium may be encapsulated (either together or separately when both are present) in microcapsules. The nanocapsules and the microcapsules may be combined in a kresi-encapsulated mixture suspended in a carrier such as water, saline, boric acid, glycerol, polyethylene glycol 400, hydroxypropyl methylcellulose, propylene glycol, or a mixture of these excipients, lubricants, or other ingredients.

Lubricant materials such as glycerol, polyethylene glycol 400, hydroxypropyl methylcellulose, or propylene glycol may provide relief for physical irritation including itchy, gritty, dry, or irritated eyes. These lubricants relieve dry eye discomfort by adding moisture in a form that persists longer than water or saline materials. These help the tear film work more effectively through their relatively high viscosity with respect to tears.

The suspending carrier may also include a vasoconstrictor or decongestant to constrict superficial blood vessels of the eye and thus reduce the appearance of redness. Suitable vasoconstrictors may include the alpha-2 agonist tetrahydrozoline HCl or oxymetazoline HCl.

Cannabinoids

In embodiments, the eye treatment compositions of the invention include cannabinoids such as CBD, full spectrum CBD, THC, or a combination of these or other cannabinoids. THC has beneficial effects in the eye at least in treating glaucoma.

CBD suppresses interleukin (IL) 8 and 10 production and induces lymphocyte apoptosis in vitro. It is a strong inhibition of neutrophil chemotaxis and modulates tumor necrosis factor (TNF)-α, IL-1, and interferon (IFN)-γ by mononuclear cells and the suppression of chemokine production by human B cells. CBD's overall effect is generally considered anti-inflammatory, though its suppression of the anti-inflammatory IL-10 suggests more complex effects. Schmuhl et al. (in *Biochemical Pharmacology*, 87: 3 pp 489-501 (2014)) reported an increase of mesenchymal stem cell migration by CBD via activation of p42/44 MAPK. Migration and differentiation of mesenchymal stem cells (MSCs) are known to be involved in various regenerative processes such as bone healing. CBD was reported to increase the migration of adipose-derived MSCs in a time- and concentration-dependent manner. Endocannabinoid (eCB) signaling has also been shown to regulate proliferation and differentiation of mesoderm-derived hematopoietic and mesenchymal stem cells, with a key role in determining the formation of several cell types in peripheral tissues, including blood cells, adipocytes, osteoblasts/osteoclasts and epithelial cells. Long-term stimulation with CBD induced differentiation of MSCs into the osteoblastic lineage as evidenced by increased mineralization. CBD may therefore recruit MSCs to sites of calcifying tissue regeneration and subsequently support bone regeneration. CBD may have similar effects on damaged tissues of the eye.

In embodiments, the invention provides cannabinoids in small capsules. This increases the effective solubility of cannabinoids by encapsulating the cannabinoid in a local lipophilic environment.

Applicants have found that cannabidiol may have beneficial effects when applied in a treatment composition for the eye including either lutein, N-acetyl carnosine, conditioned media recovered from growing cultures of stem cells, vasoconstrictors, lubricants, or some combination of these. The effects may be two-fold: first cannabidiol has direct effects on the treated tissue at various stages of the healing process. This includes reduction of inflammation, recruitment of endogenous stem cells, reduction of nociception, and support of differentiation of stem cells into end-stage cells that rebuild or remodel tissue. Second, cannabidiol may act on the recruited stem cells of the treatment composition to alter their spectrum of cell products that improves the healing effects of these cell products.

Stem Cells

A stem cell is an undifferentiated or relatively undifferentiated cell that is capable of giving rise to more cells of the same type, and from which certain other kinds of cell arise by differentiation. There are a variety of human stem cells that serve as reservoirs for recovery and replacement of damaged tissue. Many stem cell types, such as CD34-bearing hematopoietic stem cells, are known in the art. Some stem cells are difficult to harvest, but others are more readily available. For example, mobilized peripheral blood, umbilical cord blood, endothelium, adipose tissue, deciduous tooth mesenchyme, umbilical cord mesenchyme, and postpartum placenta may be collected without invasive procedures: all have all been reported as sources of stem cells.

The cells harvested as described below may not themselves be stem cells, but the harvest and subsequent processing conditions may induce some of the harvested cells or their progeny to become stem cells.

Peripheral blood may be collected through conventional venipuncture. In some instances, it may be desirable to first administer colony stimulating factors such as G-CSF (filgrastim) to increase stem cell production and mobilize stem cells from the bone marrow into the peripheral circulation. The collected cells may be fractionated by centrifugation and purified by immunomagnetic separation for $CD45^+$ cells as described in Balduini et al. in *PLoS ONE* 6(6): e21015 (2011) or for $CD34^+$ as described in Spohn et al. in *Cytotherapy*, 2015; 17: 1465-1471 using the Prodigy and CliniMACS Plus from Miltenyi Biotec. Both publications are hereby incorporated by reference for their disclosure of fractionation and purification of stem cells.

Placenta-derived stem cells (PDSCs) may be derived from post-partum placentas; no invasive procedure is necessary, since the placenta is expelled after the birth of the neonate. Yen et al. described in Stem Cells, 23: p3-9 (2005) a process wherein harvested pieces of tissue were washed several times in phosphate-buffered saline (PBS) and then mechanically minced and enzymatically digested with 0.25% trypsin-EDTA. The homogenate was subsequently pelleted by centrifugation and suspended in Dulbecco's modified Eagle's supplemented by 10% fetal bovine serum (FBS). This use of FBS may be problematic and is preferably avoided.

Adipose-derived stem cells (ADSCs) are stem cells extracted from adipose tissues. Human adipose tissue is available ex vivo as a result of cosmetic procedures including liposuction. ADSCs resemble bone marrow mesenchymal stromal cells (BMSCs): ADSCs interact with endothelial cells by expressing similar integrins to BMSCs; and, like BMSCs, ADSCs lack the dominant ligand for P-selectin. However, unlike BMSCs, providers can harvest large numbers of ADSCs with low donor-site morbidity.

Adipose tissue, like other tissue types, is not a homogenous mixture of a single cell type. Instead adipose tissue includes a combination of fat cells, vasculature, connective tissue, and blood cells. Human adipose tissue is available ex vivo as a result of cosmetic procedures including liposuction.

Stem cells may be extracted from adipose tissue by any of a number of methods known in the art, including treatment with surfactants or enzymes (including proteases such as collagenase, or trypsin), maceration, separation by centrifugation, filtering, or settling, ultrasonic treatment, adherent culturing, or some combination of these methods. Immunomagnetic separation may also be effective. Aspirated specimens from liposuction procedures (lipoaspirates) are largely composed of fat cells but also include supporting cells such as those comprising vasculature. Vascular tissue includes at least some cells identifiable as adult stem cells. Such cells bear stem cell surface markers characteristic of stem cells and detectable by flow cytometry. These cells are also capable of adherent growth in cell culture. Once extracted from adipose tissue, adipose-derived stem cells may be grown in culture by a number of methods known in the art, including growth on three-dimensional scaffolds or supports, growth in suspension culture, or growth on the surface of plastic or glass vessels.

Rodriguez et al. U.S. Pat. No. 7,531,355 B2 describes one protocol for collection and isolation of ADSCs. A hollow blunt-tipped cannula is introduced into the subcutaneous space through an about 1 cm incision. A gentle suction applied as the cannula moves through the adipose compartment mechanically disrupts and collects the fat tissue. A solution of saline and epinephrine (a vasoconstrictor) infuses into the adipose compartment to minimize blood loss and blood cell contamination of the tissue. Lipoaspirates are washed extensively with equal volumes of phosphate buffered saline (PBS) and the extracellular matrix (ECM) is digested at 37 Celsius for 30 minutes with 0.075% collagenase. In other embodiments, the enzymatic step may be replaced by sonication as described in Victor U.S. Pat. No. 8,440,440 B2. Both publications are hereby incorporated by reference for their disclosure of collection and isolation of ASDCs.

After treatment, the dissociated adipose tissue may be centrifuged. The pellet contains the stromal vascular fraction cells (SVFCs), which include ASDCs. The SVFCs may be resuspended and further washed in PBS and plated to tissue culture bottles with Dulbecco's Modified Eagle's Medium. The plated cultures may be washed to remove non-adherent cells and incubated at 37 Celsius with 5% $CO_2$. Remaining growing cells include ASDCs, which may be passaged to further enrich the division-competent cells.

Once harvested, stem cells can be at least partially purified by a number of methods. These methods include marker-based cell sorting (including by flow cytometric cell sorters or by solid phase affinity separation such as immunomagnetic beads), differential centrifugation, cell culturing with serial passaging, or dilution-based clonal isolation.

ADSCs display multipotentiality: they have the capability of differentiating at least along the adipocyte, chondrocyte, myogenic, neuronal, and osteoblast lineages. Rodriguez et al. (cited above) describes induction of multiple lineages of fate-directed cells from ASDCs. These include leiomyogenic phenotypes (including functional smooth muscle cells) from ASDCs by growth in a medium containing a transition material including 100 U/mL of heparin. Rodriguez et al. also describes techniques for production of myogenic phenotypes (by exposure to transition material including hydrocortisone in serum-rich media), of adipogenic phenotypes (by exposure to transition material including 10 µM insulin in combination with about 1 µM dexamethasone), of osteogenic phenotypes (by exposure to transition material including 1 µM dexamethasone and about 20 µM ascorbate-2-phosphate and between about 20 nM β-glycerophosphate), and neurogenic (or other ectodermal) phenotype (by exposure to transition material including 10 mM β-mercaptoethanol without serum).

Lis et al. in *Nature* published online 17 May 2017 reported conversion of adult endothelium to immunocompetent hematopoietic stem cells in mice. The process used transient expression of the transcription-factor-encoding genes and vascular-niche-derived angiocrine factors. The transduced endothelial cells committed to a hematopoietic fate. This conversion in vitro suggests that a similar conversion may occur in vivo given the appropriate microenvironment and mix of cell products.

Without intent to be bound by theory, Applicants believe that natural healing processes may include recruitment of stem cells from other cells such as endothelium cells and differentiation of stem cells into multiple lineages. The boundary between what is and what is not a multipotent stem cell may be blurred by such recruitment, conversion, and differentiation. To take maximal advantage of healing potential requires providing the appropriate microenvironment. Applicants believe that this microenvironment may be supported by stem cell products and particularly stem cell products in the presence of cannabidiol at the site of healing.

Stem Cell Culture

Once extracted from tissue, stem cells may be grown in tissue culture by a number of methods known in the art, including growth on three-dimensional scaffolds or supports, growth in suspension culture, or growth on the surface of plastic or glass vessels.

Culture of cells for human use must take place under sterile conditions with particular attention paid to avoiding contamination by infectious organisms, including those infecting the stem cell donors. Contamination may also arise from culture materials: for example, use of serum products, such as bovine fetal calf serum (FCS), is very common in cell culture. Serum products contain an uncontrolled mixture of components that may interact with stem cells. For example, FCS may contain variable amounts of endocannabinoids such as anandamide or other ligands capable of activating the peripheral cannabinoid receptors. In embodiments, the invention provides treatment compositions derived from human cells that have not been cultured in the presence of or exposed to serum products.

Human cultured cells, including stem cells and their progeny, produce a variety of growth-promoting and healing materials such as growth factors, cytokines, stress proteins, and nutrients including TGF-B, PDGF, and GM-CSG, interleukins, and matrix proteins (collectively, cell products). While many of these have been identified, stem cells likely also secrete other substances either not yet known or with beneficial functions yet to be precisely identified. Some of these materials may be effective at low concentration.

Human stem cells, such as ASDCs, produce a variety of growth-promoting and healing materials such as growth factors and cytokines. These mixtures of cell products may be harvested from cultured cells by collecting the culture medium to which such cells have been exposed.

Growth of such cultured stem cells includes supply of nutrients for the cells through provision of an aqueous culture medium. Cells grow in culture in contact with medium and extract nutrients from it. These cells also deliver to the medium products of their growth and metabolism. Among the products are the growth factors and cytokines discussed above as well as metabolic products. Conventional cell culture requires replacement of culture medium as cells use up nutrients and deliver products that may affect future cell growth. This replacement may be either continuous, with a portion of the medium removed as new medium is added, or intermittent with periodic replacement of some or all of the culture medium in a vessel. Culture medium removed after exposure to cells in culture is known as spent or conditioned medium.

Stem Cell-Conditioned Medium

As discussed above, growth of cells such as adipose-derived stem cells includes supply of nutrients for the cells through provision of an aqueous culture medium. Cells grown in culture deliver to the medium cell products including growth factors and cytokines as well as metabolic products. Culture medium removed after exposure to cells includes stem cell products as well as residual components of the original medium, such as essential amino acids, salts, vitamins, minerals, trace metals, sugars, lipids, and nucleosides. Cell culture medium attempts to supply the components necessary to meet the nutritional needs required to grow cells in a controlled, artificial and in vitro environment. Nutrient formulations, pH, and osmolarity may vary depending on the type of cell cultured, on cell density, and on the culture system employed. The scientific literature includes description of many cell culture medium formulations; a number of such media are commercially available. Conditioned medium also contains a variety of cellular metabolites and secreted proteins, including, for example, biologically active growth factors, inflammatory mediators and other extracellular proteins. Examples of suitable culture media are Dulbecco's Modified Eagle's Medium and RPMI 1640. Such media may be supplemented by other nutrients, growth supporting materials, or antibiotics as is known in the art.

Without intent to be bound by theory, Applicants believe that endogenous regenerative cells have a limited ability to restore function to impaired tissue, particularly where the impairment is age-related. Reduced blood flow and vascular supply to the impaired region and declining hormone levels may further inhibit recuperative mechanisms. The provision of more adequate perfusion may facilitate more complete recovery by endogenous regenerative cells. Exogenous stem cell products of the conditioned media may participate in healing by increasing the rate of collagen secretion, vascular ingrowth and fibroblast proliferation. Improved vascular ingrowth may further potentiate healing of an affected area by giving better vascular access.

Compositions of the invention may include stem cell-conditioned media to deliver payloads of tailored growth factors. These may serve to restore the activity of endogenous regenerative cells and may further serve to recruit and convert new stem cells during treatment. These cells may contribute to recovery and repair of the impaired tissues and restoration of full function.

In some embodiments, conditioned medium may also contain added ingredients such as antimicrobials, added growth factors, peptides, or acellular extracellular matrix.

Encapsulation

In embodiments, components of the treatment compositions may be encapsulated. Encapsulation can protect active agents from the surrounding environment and may protect sensitive eye tissues against irritation. Encapsulation may also serve to control the release of active materials to a desired time (e.g. when exposed to a particular environment in the eye) or at a desired rate. Conventional encapsulation processes, such as encapsulation by liposomes may be used, as well as other methods known in the art, including those reviewed by Yadav et al. in Peptides 32 pp. 173-187 (2011). This review is hereby incorporated by reference for its disclosure of methods of encapsulation.

Encapsulation processes differ in the size of the capsules produced. When capsules are in the range of about 500 nm to roughly cellular dimensions of about 10 μm, the product is microencapsulated. When capsules are in the range of about 20 nm to 500 nm the product is nanoencapsulated. These are largely terms of convenience since capsules are usually not monodisperse but have a range of sizes. An encapsulated product where the capsules are prepared in a common process may be characterized by a size distribution having a median capsule diameter. For the purposes of this document, such capsules are microencapsulated if the median diameter of the capsules is in the microencapsulated range and are nanoencapsulated if the median diameter of the capsules is in the nanoencapsulated range.

Capsules prepared in more than one process or in more than one batch may be combined where one of the sets of capsules are microencapsulated and another of the sets of capsules are nanoencapsulated. Such mixed capsule distributions will be referred to as kresi-encapsulated (a coinage from the Greek Κρασις meaning mixing or blending).

In embodiments, CBD (or other cannabinoids or mixture of cannabinoids such as full spectrum CBD), or a mixture of such cannabinoids with lipophilic materials including lutein, may be encapsulated in nanocapsules. The smaller nanocapsules size range is preferred for these lipophilic materials in part because their density differs significantly from water. Larger capsules have a greater propensity to float or sink because their behavior is more subject to large scale forces such as buoyancy. Smaller nanocapsules are more likely to remain in suspensions as their behavior is dominated by small scale forces such as diffusion and Brownian motion. Nano-sized particles may also retain a small surface charge that may be sufficient to repel similar particles and help maintain them in suspension.

Exemplary nanocapsules include liposomes and polymer nanocapsules.

Liposomes contain one or more lipophilic surfactants such as dipalmitoylphosphatidylcholine or phosphatidylinositol. Cholesterol may be added as a further liposome component to improve stability. Dipalmitoylphosphatidylcholine is a phospholipid consisting of two palmitic acids attached of a phosphatidylcholine head-group. Phosphatidylinositol is a phosphatidylglyceride including an inositol group. These materials are merely illustrative of a class of lipophilic surfactants such as occur in cell membranes. These materials have been reported to be useful to prepare liposomes containing CBD (see, for example, Hung, et al. PCT publication WO 01/03668, incorporated by reference for its teaching of liposome encapsulation of cannabinoids). One or more of these lipophilic surfactant materials (or a mixture of the materials with cholesterol) may be mixed with CBD (or CBD plus lutein) in organic solvent with CBD forming between 0.5 and 10% of the weight of the mixture. After drying the solvent, the residue may be mixed with phosphate buffered saline (120 mM, pH 7) and extruded through 400 nm pore sized polycarbonate filters to form liposomes.

The size of the liposomes produced depends on mechanical parameters of the process, such as the pore size of the filters and the flow rate through the pores. Size distribution may be adjusted by varying these parameters.

In other embodiments, CBD or other cannabinoids are prepared in polymer capsules. The materials used for encapsulation with polymers may be selected from conventional hydrophilic or hydrophobic substances or mixtures thereof. Solids, in particular natural polymers, for example, starch and other polysaccharides, or zein or other proteins, are preferred because of their biocompatibility. However, synthetic polymers can also be used. Examples of shell materials are fats and/or waxes, preferably those having a solidification temperature of approximately 35-80 Celsius and include mixtures of cetyl palmitate and cetyl alcohol. Other compounds include: polysaccharides and their derivatives of natural or partially synthetic origin, (e.g. cellulose derivatives); polymers of γ- and/or β-hydroxycarboxylic acids, in particular polymers of glycolic acid (polyglycollides), lactic acid (polylactides), γ-hydroxybutyric acid (polyhydroxybutyrate), γ-hydroxyvaleric acid (poly (3-hydroxyvalerate) and/or their copolymers, or mixtures of such polymers and/or copolymers.

A suitable method of encapsulation includes emulsification polymerization using aqueous phase methacrylate monomer and a photoinitiator such as benzoin ethyl ether (dissolved in organic phase components or emulsified in aqueous phase components) with polyethylene oxide as a stabilizer and exposure to UV light after emulsification to produce poly(methacrylate) encapsulated active components. The capsules may range from about 50 to about 5000 nm in diameter, depending on the precise conditions used. In some embodiments, washed capsuled may be size selected by filtration, sedimentation, or similar methods. Other suitable methods include interface condensation where reactive monomers are separately dispersed in aqueous and lipophilic phases Hydroxy methylcellulose or other polysaccharides or zein, albumin, gelatin or other proteins core-shell capsules may be prepared by a coacervation technique. The shell material is dissolved in an aqueous solvent in a colloidal or a true solution. The core material to be packaged (cannabinoid with or without lutein) is dissolved in a suitable organic solvent such as coconut oil or food grade mineral oil. This is dispersed with in the form of solids or microdroplets. The dispersion may be divided into micro or nano-droplets and then heated with hot air or dried under reduced pressure. The aqueous solvent evaporates and the shell material reprecipitates in as a solid or gel, forming a shell around the core material. Again, the capsule size range depends on the precise conditions used in a manner familiar to those skilled in the art.

Preferred size range for liposomes or other capsules containing cannabinoids or cannabinoids plus lutein is in the range of about 50 nm to about 500 nm. In some embodiments, the range may about 100 nm to about 250 nm. This narrower size range beneficially delivers a more consistent dosing over time. Dose delivery is controlled by diffusion of particles through the aqueous environment of the eye and suspending liquid. A narrower range of sizes has more consistent rate of diffusion between liposomes. Further, smaller particles divide the total dose of packaged materials into more liposomes, thereby decreasing the average distance between liposomes and reducing diffusion time.

A benefit of the encapsulation of CBD (or other cannabinoid or cannabinoid mixture with or without lutein) is that more CBD may be delivered in a substantially aqueous suspension. A further benefit is that the encapsulated CBD may gradually extract from the capsules, making the CBD available in solution over an extended time. A still further benefit that the encapsulated material acts as a reservoir to "buffer" the CBD concentration in the in contact with tissue to a relatively constant sustained value.

In other embodiments, microencapsulated aqueous components such as stem cell-conditioned medium (with or without added antioxidants such as N-acetyl carnosine, glutathione, or ascorbic acid) may be prepared by similar methods to that described above for polymer capsules containing lipophilic materials except that the phases are reversed so that the to be encapsulated materials are dispersed in the aqueous phase. The size may be adjusted by varying the physical parameters such as proportion of lipophilic to hydrophilic phases, mixing stringency for coacervation techniques, or emulsification parameters for emulsification polymerization or interface polymerization.

Microencapsulated aqueous components such as stem cell-conditioned medium (with or without added antioxidants such as N-acetyl carnosine, glutathione, or ascorbic acid) may also be prepared as narrow size distribution using the apparatus and method described in US patent publication 2008/0182019 entitled Hollow Microsphere Particle Generator. This publication is hereby incorporated by reference for its disclosure of methods of microencapsulation of aqueous phase materials.

Regardless of the method of encapsulation selected, microcapsules containing aqueous components such as stem cell-conditioned medium, N-acetyl carnosine, or a combination of enriched stem cell medium and N-acetyl carnosine are preferably in the size range of 500 nm to about 5 µm. This larger size range for the aqueous materials is preferred because their density is close to that of a suspending aqueous liquid, enabling the capsules to remain substantially neutrally buoyant. At least in the case of stem cell-conditioned medium, the concentration of active materials may be relatively low, so that larger capsules may be needed to deliver an effective dose. Further, the delivery of these larger sized capsules may be timed with respect to that of the smaller nanoencapsulated lipophilic materials by the method of administration. Larger capsules are more affected by surface tension and mechanical motion such as produced by blinking and tearing in the eye. The effect of this is that larger capsules have a shorter effective lifetime in the eye than do nanocapsules, with capsules that do not "land" on a tissue surface are washed away. The smaller nanoencapsulated lipophilic materials behave more like a bulk fluid and are not so easily washed out by mechanical action. The combination thus may provide an early large pulse of hydrophilic components followed by a more sustained release of lipophilic materials.

The size of the capsules may also be mechanically limited by anatomy of the eye, with smaller particles able to reach regions not accessible to the larger particles. The value of this depends on the condition to be treated. In some embodiments, the size of capsules may be adjusted to optimize access to a targeted treatment site.

Encapsulated components may be washed by dialysis, by centrifugal filtration, by tangential flow filtration, by centrifugation and decanting, or by other techniques known in the art, to produce washed encapsulated components. Washing helps remove unreacted monomers or initiator as well as materials not incorporated in capsules. Alternatively, and depending on the materials used in the encapsulation process, encapsulated components may be used without further processing. After washing, encapsulated components may be resuspended in a buffer, in sterile saline, in water, or in a suspension containing other excipient materials. In some embodiments, the encapsulated components may be mixed with other encapsulated components to produce a mixture of encapsulated species; the mixed capsules may differ in size distributions and may be a kresi-encapsulated mixture.

Regardless of the selected technique for preparing capsules, the processes used should be at a temperature that does not cause the components of the formulation to decompose or lose significant activity.

The invention includes a method of treating an eye by applying one or more compositions of the invention in the form of eye drops. In embodiments, an effective amount of one of the compositions described above is applied to the eye in one or a few droplets. The treatment may be repeated at intervals.

Direct delivery of therapeutic compositions to affected tissue may be preferred over the systemic delivery of such compositions for several reasons related to concentration of the compositions. A substantially greater concentration of such compositions can be delivered directly into affected tissue, compared with the dilute concentrations possible through systemic delivery. Systemic administration may be associated with systemic toxicity at doses required to achieve effective concentrations in the affected tissue.

Direct delivery to the eye generally means topical administration or injection. The eye is particularly sensitive to pain, so that the mere thought of injections induces cringes. Eye drops are far less invasive and hence preferred, provided they effectively deliver therapeutic composition in a well-tolerated way. The compositions of the invention may be modified for topical application to keep the material in place, such as by addition of thickening agents such as methyl cellulose. In other embodiments, the composition may be applied with a dressing that retains the composition in place for a treatment period.

Application of eye drops is not without discomfort, even though much less so than injections. Because CB2 receptor agonists have been shown to modulate acute pain, Applicants believe that the provision of CBD in treatment compositions may reduce discomfort of treatment.

To the extent that injury, healing, or treatment may result in pain at the site, CBD may serve to reduce such pain because of a combination of anti-inflammatory and pain-relieving properties.

Example 1

Volunteer subjects reporting symptoms of eye redness, dryness, itchiness, puffiness, or tearing were provided with an eye treatment composition including nanoencapsulated CBD and other disclosed components for self-treatment. Subjects included ten males and females between ages 25 and 62. Each subject applied two drops of the composition to each affected eye when symptoms developed. Subjects noted the severity of the symptom suffered and recorded the effectiveness of symptom relief at 15 minutes post-treatment. Subjects evaluated symptom relief using a five-point scale, with a score of 1 indicating high effectiveness and a score of 5 indicating no symptom relief. Subjects were instructed to reapply the composition if needed up to a maximum of three times per day. The trial continued for five days with subjects applying the composition only when symptoms developed.

Table 1 shows a summary of results for each symptom.

| Symptom | Total Coccurrences | reported scores | | | | | mean score | # of subjects |
| --- | --- | --- | --- | --- | --- | --- | --- | --- |
| | | 1 | 2 | 3 | 4 | 5 | | |
| redness | 27 | 26 | 1 | | | | 1.04 | 9 |
| dryness | 34 | 16 | 17 | 1 | | | 1.56 | 8 |
| itchiness | 8 | 1 | 5 | 2 | | | 2.13 | 2 |
| puffiness | 1 | 1 | | | | | 1 | 1 |
| tearing | 4 | 2 | 2 | | | | 1.5 | 1 |

The results show that the eye treatment composition, when applied topically as eye drops, provided effective symptom relief to the subjects. The composition was most effective at the test dosage for eye redness (mean of 1.04; N=27). Eye puffiness only occurred once, but the treatment was highly effective in that instance. The composition was effective to a lesser degree against eye tearing (mean of 1.5;

N=4) and eye dryness (mean of 1.56; N=34). The treatment had moderate effectiveness against eye itchiness (mean of 2.13; N=8). The study thus demonstrates at least some effectiveness of the treatment compositions applied as eye drops for these conditions.

The embodiments described herein are referred in the specification as "one embodiment," "an embodiment," "another embodiment," etc. These references indicate that the embodiment(s) described can include a particular feature, structure, or characteristic, but every embodiment does not necessarily include every described feature, structure, or characteristic. Further, when a particular feature, structure, or characteristic is described in connection with an embodiment, such feature, structure, or characteristic in may also be used in connection with other embodiments whether or not explicitly described.

Further, where specific examples are given, the skilled practitioner may understand the particular examples as providing particular benefits such that the invention as illustratively disclosed herein suitably may be practiced in the absence of any element which is not specifically disclosed herein or within that particular example. As a non-limiting example, the disclosed embodiments may benefit from the exclusion of certain materials, such as any of the list of anti-inflammatory agents in Morariu cited above. These anti-inflammatory agents may in some circumstances conflict with the action of some ingredients of the stem cell-conditioned medium. This disclosure in embodiments also contemplates the combination of an encapsulated cannabinoid together with a lutein, a lubricant, a vasoconstrictor, and N-acetyl carnosine. It is expressly within the scope of the disclosure that embodiments of the invention may exclude any of these or other recited ingredients so that a claim may be limited to not include any such ingredient. It is also expressly within the scope of the disclosure that some embodiments may specifically exclude certain cannabinoids, such as excluding THC to avoid psychoactive effects.

Each of the references cited in this disclosure are hereby incorporated by reference. This disclosure also mentions certain other documents incorporated by reference. Where such documents conflict with the express disclosure of this document, this document controls.

Although the present disclosure describes certain exemplary embodiments, it is to be understood that such disclosure is purely illustrative and is not to be interpreted as limiting. Consequently, without departing from the spirit and scope of the disclosure, various alterations, modifications, and/or alternative applications of the disclosure will, no doubt, be suggested to those skilled in the art after having read the preceding disclosure. Accordingly, it is intended that the following claims be interpreted as encompassing all alterations, modifications, or alternative applications as fall within the true spirit and scope of the disclosure.

We claim:

1. An eye treatment composition comprising:
a first plurality of nanocapsules;
a plurality of microcapsules;
a cannabinoid dispersed in the first plurality of nanocapsules;
N-acetyl carnosine dispersed in the plurality of microcapsules;
an aqueous carrier, the first plurality of nanocapsules and the plurality of microcapsules suspended in an aqueous carrier; and
lutein dispersed in a second plurality of nanocapsules.

2. A method of treating an eye condition comprising applying an effective amount of the eye treatment composition of claim 1 to an affected eye.

3. The eye treatment composition of claim 1, wherein the first plurality of nanocapsules has a median size in the range of 50 to 250 nm, and wherein the plurality of microcapsules has a median size in the range of 500 nm to 5 μm.

4. The eye treatment composition of claim 1, wherein the first plurality of nanocapsules further contains a lutein co-dispersed with the cannabinoid.

5. The eye treatment composition of claim 1, wherein the aqueous carrier includes a vasoconstrictor and a lubricant.

6. The eye treatment composition of claim 5, wherein the lubricant has one or more of glycerol, polyethylene glycol 400, hydroxypropyl methylcellulose, or propylene glycol.

7. The eye treatment composition of claim 1, wherein the cannabinoid includes cannabidiol (CBD) or tetrahydrocannabinol (THC).

8. An eye treatment composition comprising:
a first plurality of nanocapsules including a cannabinoid dispersed in the first plurality of nanocapsules;
a second plurality of nanocapsules including lutein dispersed in the second plurality of nanocapsules; and
an aqueous carrier, the first plurality of nanocapsules and the second plurality of nanocapsules suspended in the aqueous carrier.

9. The eye treatment composition of claim 8, wherein the first plurality of nanocapsules has a median size in the range of 50 to 250 nm.

10. The eye treatment composition of claim 8, wherein the cannabinoid includes cannabidiol (CBD) or tetrahydrocannabinol (THC).

11. The eye treatment composition of claim 8, further comprising an aqueous antioxidant mixed with the aqueous carrier.

12. The eye treatment composition of claim 8, further comprising a lubricant or a vasoconstrictor mixed with the aqueous carrier.

13. The eye treatment composition of claim 8, further comprising a stem cell conditioned medium mixed with the aqueous carrier.

14. The eye treatment composition of claim 8, further comprising a plurality of microcapsules encapsulating a conditioned medium, wherein the conditioned medium is derived from a culture of one or more of a human hematopoietic stem cell, a human endothelium-derived stem cell, a human adipose-derived stem cell, a human tooth mesenchyme-derived stem cell, or a human placenta-derived stem cell.

15. The eye treatment composition of claim 14, wherein the aqueous carrier includes a lubricant.

16. The eye treatment composition of claim 15, wherein the aqueous carrier includes a vasoconstrictor.

17. The eye treatment composition of claim 16, wherein the first plurality of nanocapsules further contains lutein co-dispersed with the cannabinoid.

18. The eye treatment composition of claim 17, wherein the aqueous carrier includes N-acetyl carnosine.

* * * * *